(12) United States Patent
Dubois et al.

(10) Patent No.: US 11,442,026 B2
(45) Date of Patent: *Sep. 13, 2022

(54) CRACK STRUCTURE AND TUNNELING DEVICE WITH A LAYER EXHIBITING A CRACK-DEFINED GAP BETWEEN TWO CANTILEVERING PARTS

(71) Applicant: Zedna AB, Täby (SE)

(72) Inventors: Valentin Dubois, Stockholm (SE); Frank Niklaus, Täby (SE); Göran Stemme, Lidingö (SE)

(73) Assignee: Zedna AB, Täby (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/947,831

(22) Filed: Aug. 19, 2020

(65) Prior Publication Data

US 2020/0378902 A1  Dec. 3, 2020

Related U.S. Application Data

(62) Division of application No. 16/062,517, filed as application No. PCT/EP2016/081019 on Dec. 14, 2016, now Pat. No. 10,782,249.

(30) Foreign Application Priority Data

Dec. 14, 2015 (SE) .................................... 1500508-5
May 17, 2016 (SE) .................................... 1600167-9
Sep. 9, 2016 (SE) .................................... 1600253-7

(51) Int. Cl.
*C12Q 1/6869* (2018.01)
*G01N 27/327* (2006.01)
(Continued)

(52) U.S. Cl.
CPC ....... *G01N 21/9505* (2013.01); *C12Q 1/6869* (2013.01); *G01N 27/3278* (2013.01);
(Continued)

(58) Field of Classification Search
CPC ........... G01N 21/9505; G01N 27/3278; G01N 33/48721; H01L 22/12; H01L 21/302;
(Continued)

(56) References Cited

U.S. PATENT DOCUMENTS 5,490,034 A   2/1996  Zavracky et al.
5,862,275 A   1/1999  Takeuchi et al.
(Continued)

FOREIGN PATENT DOCUMENTS

EP    2 833 126 A1    2/2015
KR    101 489 154 B1  2/2015
(Continued)

OTHER PUBLICATIONS

International Search Report, dated Mar. 31, 2017, from corresponding PCT application No. PCT/EP2016/081019.
(Continued)

*Primary Examiner* — Sang H Nguyen
(74) *Attorney, Agent, or Firm* — Faegre Drinker Biddle & Reath LLP

(57) ABSTRACT

Disclosed is a method of making a crack structure on a substrate, the crack structure being usable as a tunnelling junction structure in a nanogap device, including the controlled fracture or release of a patterned layer under built-in stress, thereby forming elements separated by nanogaps or crack-junctions. The width of the crack-defined nanogap is controlled by locally release-etching the film at a notched bridge patterned in the film. The built-in stress contributes to forming the crack and defining of the width of the crack-defined nanogap. Further, by design of the length of the
(Continued)

bridge in a range between sub-µm to >25µm, the separation between the elements, defined by the width of the crack-defined nanogaps, can be controlled for each individual crack structure from <2 nm to >100 nm. The nanogaps can be used for tunneling devices in combination with nanopores for DNA, RNA or peptides sequencing.

13 Claims, 4 Drawing Sheets

(51) Int. Cl.
　　　H01L 21/02　　　(2006.01)
　　　H01L 21/66　　　(2006.01)
　　　H01L 21/302　　(2006.01)
　　　G01N 21/95　　　(2006.01)
　　　G01N 33/487　　(2006.01)
　　　B82Y 5/00　　　　(2011.01)
　　　B82Y 15/00　　　(2011.01)
　　　B82Y 40/00　　　(2011.01)

(52) U.S. Cl.
　　　CPC . *G01N 33/48721* (2013.01); *H01L 21/02603* (2013.01); *H01L 21/302* (2013.01); *H01L 22/12* (2013.01); *B82Y 5/00* (2013.01); *B82Y 15/00* (2013.01); *B82Y 40/00* (2013.01)

(58) Field of Classification Search
　　　CPC .. H01L 21/02603; C12Q 1/6869; B82Y 15/00
　　　See application file for complete search history.

(56) References Cited

U.S. PATENT DOCUMENTS

| | | |
|---|---|---|
| 7,686,907 B1 | 3/2010 | Woolley et al. |
| 8,247,214 B2 | 8/2012 | Sowerby et al. |
| 9,068,914 B2 | 6/2015 | Shim et al. |
| 9,683,956 B2 | 6/2017 | Lim |
| 10,782,249 B2 | 9/2020 | Dubois et al. |
| 2003/0230798 A1* | 12/2003 | Lin .................. H01L 24/11 257/704 |
| 2004/0016995 A1* | 1/2004 | Kuo .................. B81C 1/0023 257/678 |
| 2004/0072057 A1 | 4/2004 | Beatty et al. |
| 2006/0239635 A1 | 10/2006 | Zalalutdinov et al. |
| 2007/0023851 A1 | 2/2007 | Hartzell et al. |
| 2007/0187744 A1 | 8/2007 | Kreupl |
| 2007/0241655 A1 | 10/2007 | Sakemura et al. |
| 2009/0283751 A1 | 11/2009 | Yang et al. |
| 2010/0112493 A1 | 5/2010 | Adelung et al. |
| 2010/0248484 A1 | 9/2010 | Bower et al. |
| 2010/0303687 A1 | 12/2010 | Blaga et al. |
| 2011/0043937 A1 | 2/2011 | Juncker et al. |
| 2011/0047785 A1 | 3/2011 | Biskeborn et al. |
| 2011/0227558 A1 | 9/2011 | Mannion et al. |
| 2012/0114868 A1* | 5/2012 | Bunker ............... B23P 15/04 427/448 |
| 2013/0032210 A1 | 2/2013 | Johnstone et al. |
| 2013/0186925 A1 | 7/2013 | West et al. |
| 2014/0048851 A1 | 2/2014 | Wernersson et al. |
| 2014/0055150 A1 | 2/2014 | Kawai et al. |
| 2014/0125310 A1 | 5/2014 | Lee et al. |
| 2014/0377579 A1 | 12/2014 | Ren et al. |
| 2015/0309229 A1 | 10/2015 | Ren et al. |
| 2016/0341688 A1 | 11/2016 | Lim |
| 2017/0131237 A1 | 5/2017 | Ikeda |
| 2017/0162447 A1 | 6/2017 | Glass et al. |
| 2018/0372653 A1 | 12/2018 | Dubois et al. |
| 2021/0239625 A1 | 8/2021 | Dubois et al. |

FOREIGN PATENT DOCUMENTS

| | | |
|---|---|---|
| WO | 2011/103424 A2 | 8/2011 |
| WO | 2011/103424 A3 | 10/2011 |
| WO | 2015/199455 A2 | 12/2015 |
| WO | 2015/199455 A3 | 3/2016 |

OTHER PUBLICATIONS

Fernández-Martínez et al., "Parallel nanogap fabrication with nanometer size control using III-V semiconductor epitaxial technology", Nanotechnology, May 27, 2008, vol. 19, IOP Publishing Ltd, 6 pages.

* cited by examiner

CRACK STRUCTURE AND TUNNELING DEVICE WITH A LAYER EXHIBITING A CRACK-DEFINED GAP BETWEEN TWO CANTILEVERING PARTS

The present invention relates to crack structures in or on substrates in general, and in particular to so called crack junctions, usable as electronic nanogaps and tunnelling junctions i.a. in devices for DNA sequencing.

BACKGROUND OF THE INVENTION

Electronic nanogaps feature rich physics and are fundamental building blocks in a wide range of application areas as described in Dubois, V., Niklaus, F. & Stemme, G. Crack-Defined Electronic Nanogaps. Advanced Materials 28, 2178-2182, doi:10.1002/adma.201504569 (2016), incorporated herein in its entirety by reference. Nanogap applications can be divided into: (i) applications using electron transport mechanisms such as tunnel junctions and Josephson junctions if superconductive electrodes are employed; (ii) applications using strong light-matter interactions such as plasmonic biosensors; (iii) applications using mechanical tuning of the nanogap width such as nanoelectromechanical switches and mechanically tunable nanophotonics and; (iv) applications using magnetic interactions by employing magnetic electrodes such as fundamental scientific studies. One important advantage of free-space nanogaps between electrode surfaces, as opposed to electrodes separated by an insulating solid-state material, is that nano-objects such as molecules can be introduced inside the nanogap. This facilitates investigations of electron transport mechanisms and light-matter interactions in a large variety of configurations.

Scanning tunneling microscopy (STM) remains a preferred platform for the study of fundamental atomic-scale charge transport phenomena and electromagnetic field effects. However, it is very challenging to integrate a large number of STM tips on a chip and use the individual tips to perform atomic-scale functions within a complex system. On-chip integrated electronic nanogaps are a promising alternative to study and utilize the atomic-scale effects, described by Dubois et al. A number of fabrication techniques to realize electronic nanogaps are available and Dubois et al provides a comparison of common approaches with their advantages and limitations. None of the previously reported techniques, however, can achieve the scalability and extreme geometries obtainable in crack-defined electronic nanogaps. For instance, Dubois et al illustrates the break junction (BJ) approach, which can generate individual, atomically sharp electrode tips with sub-1 nm separations. Break junctions are formed either by applying a mechanical force to a substrate, e.g. by using a piezo-motor to bend the substrate and pull ductile electrodes apart until breaking, by electromigration that is utilizing the force from the flow of electrons to displace atoms out of a constriction in an electrode bridge until a Break junction is formed, or by FIB milling to induce grain boundary Break junctions. Control of the inter-electrode spacing in Break junctions is achieved by mechanical bending of the entire substrate, resulting in precise displacements of the electrodes. While Break junctions are interesting from many respects, only a few Break junctions can be simultaneously fabricated on a substrate, thereby rendering them unsuitable for applications requiring a larger number of Break junctions on a chip, such as complex molecular electronic circuits.

Dubois et al illustrate the nanogap fabrication approach using masking layers in combination with etching processes. The dimensions and shape of the nanogap and electrodes are defined in a masking layer on top of the electrode layer, which is then used to pattern the electrode layer by anisotropic etching. Therefore, the masking layer must resolve accurately the nano-scale features defining the nanogap, which is technologically very challenging for sub-10 nm dimensions. The pattern transfer by etching further deteriorates the precision of the features and severely limits the obtainable gap-height to gap-width aspect-ratios. FIG. S2d illustrates nanogap fabrication approaches using sacrificial spacer layers to define gap widths. In these methods, a thin sacrificial spacer layer is deposited on top of an electrode. Next, the second electrode is deposited and patterned. Finally, the spacer layer is sacrificially removed using isotropic chemical etching to form a nanogap separating the electrodes. The width of the nanogap is defined by the thickness of the sacrificial layer, which can be controlled very accurately. However, this approach is not suitable for fabricating several nanogaps with different gap widths on a substrate. Furthermore, the need for etching the sacrificial layer inside extremely narrow nanogaps is limiting the obtainable gap-height to gap-width aspect-ratios and bears risks for etch-residues to contaminate the electrode surfaces. Such etch-residues can significantly affect the electrical or optical properties of a nanogap, especially in sub-10 nm wide gaps where the dimension is counted in a few tens of atoms. FIG. 2e illustrates nanogap fabrication approaches using material growth that is narrowing existing gaps. Therefore, a comparably wide gap is formed, e.g. by lithographic patterning. This gap is then narrowed down by depositing additional electrode material. Suitable deposition processes include chemical and electrochemical deposition, and shadow mask evaporation. When using deposition processes such as electroplating to realize sub-10 nm wide gaps, the gap width of each individual nanogap device has to be monitored by continuous electrical feedback during the deposition processes, which severely limits the scalability of these approaches. When using deposition processes such as oblique evaporation with shadow masks, the process and geometry control is extremely challenging and the reproducibility and achievable yield is limited.

WO2015199455A3 discloses a method for producing a nanogap sensor by using a technique of forming a micro crack on a substrate consisting of a silicon wafer, etc., and then stacking a metal catalyst layer on the nanogap.

WO2011103424A3 discloses background technology for nanopores in synthetic membranes used for DNA sequencing.

U.S. Pat. No. 7,686,907 discloses a microchip with capillaries and method for making same is described. A sacrificial material fills microchannels formed in a polymeric substrate, the filled microchannels are covered by a top cover to form filed capillaries, and the sacrificial material is removed to form the microcapillaries. The sacrificial material fills the microchannels as a liquid whereupon it becomes solid in the microchannels, and is liquefied after the top cover is applied and affixed to remove the sacrificial material. The top cover may be solvent sealed on the substrate and of the same or different material as the substrate. The top cover may also be an in situ applied semipermeable membrane.

US20090283751A1 discloses a device with nanopores. Electrodes on opposing sides of the nanotube establish electrical contact with the fluid therein. A bias current is passed between the electrodes through the fluid, and current changes are detected to ascertain the passage of select molecules, such as DNA, through the nanotube.

EP2833126A1 shows how a nanopore/gap can be formed through break junction techniques.

U.S. Pat. No. 8,247,214 discloses a method for detecting, measuring or controlling particles and/or electromagnetic radiation, comprising providing a deformable material containing a deformable aperture defining a path for particles or radiation, adjusting the deformable aperture to a prescribed geometry and/or size by deforming the deformable material to change at least one of the parameters of the path defined by the deformable aperture.

US20110227558A1 describes prior art techniques for an electrical detector comprising a nanofluidic channel.

US 20140125310 A1 discloses a nanogap device which includes a first insulation layer having a nanopore formed therein, a first nanogap electrode which may be formed on the first insulation layer and may be divided into two parts with a nanogap interposed between the two parts, the nanogap facing the nanopore, a second insulation layer formed on the first nanogap electrode, a first graphene layer formed on the second insulation layer, a first semiconductor layer formed on the first graphene layer, a first drain electrode formed on the first semiconductor layer, and a first source electrode formed on the first graphene layer such as to be apart from the first semiconductor layer.

US 20130186925 A1 discloses a method of patterning an electrically-conductive film is performed by providing a flexible substrate that carries the electrically-conductive film thereon to form a combined layer. The combined layer is then bent about a radius of curvature, so as to impart a stress on the brittle conductive film along the axis of curvature of the curved surface. The application of the stress to the conductive film results in the formation of crack lines that are substantially perpendicular to the direction to which the substrate and conductive film are bent. The crack lines serve to define and electrically isolate conductive sections therebetween that can be utilized as electrodes and address lines in electronic devices.

The above cited documents are all incorporated herein in their entirety.

SUMMARY OF THE INVENTION

The object of the present invention is to provide crack structures in substrates, e.g. in semiconductor or glass substrates, usable as nanogap structures or as tunnelling junctions, i.e. electrode-pairs with a sub-3 nm nano-scale gap, for use in various types of devices.

This object is met in a first aspect by the method defined in claim 1.

Thus, the method of forming a crack structure on a substrate, comprises the steps of providing a substrate and providing a sacrificial layer on the substrate. Then a layer of one or more selected materials is provided on the sacrificial layer, such that there will be a built-in stress in the material. The layer of selected material(s) is patterned, suitably using lithography involving masking and etching, to provide a bridge, preferably elongated, having one or several stress concentration structures, preferably a notch or notches located opposite each other along longsides of said bridge or as grooves extending across the bridge. Etching away the sacrificial layer beneath at least part of the bridge will cause the bridge to crack at the stress concentration structures due to release of the built-in stress, thus defining a crack structure, provided the built-in stress is appropriate. However, it is possible to set the built-in stress such that the crack forms before etching away the sacrificial layer. The built-in stress can also be set such that the crack forms only after the sacrificial layer has been etched away. The width of the crack-defined gap is predetermined by the length of the bridge and the built-in stress.

Preferably, the built-in stress is achieved by the selected material(s) having a different coefficient of thermal expansion than the substrate material, and wherein the deposition of the material is performed at temperature(s) that is different from the temperature at which the crack is formed.

In a further embodiment the substrate is preferably made from a material, selected from the group consisting of Si, silicon carbide, glass, quartz, sapphire, GaN, GaAs, InP, and polymer. In particular the substrate can be a single crystal Si wafer containing CMOS integrated circuits.

The sacrificial material preferably selected from the group consisting of $Al_2O_3$, Si, SiO2, SiN, Al, single or few-layer graphene, and polymer, preferably provided by deposition techniques including, any of atomic layer deposition (ALD), sputtering, evaporation, chemical vapor deposition (CVD), layer transfer, spray coating, spin coating, and epitaxial growth.

The layer of material(s) preferably comprises a stacked structure of one or several electrically conductive layers separated by one or several dielectric layers and, wherein the conductive material preferably consisting of gold, platinum, single or few-layer graphene, titanium nitride, and superconducting materials, preferably provided by deposition techniques including, any of atomic layer deposition (ALD), sputtering, evaporation, chemical vapor deposition (CVD), layer transfer, spray coating, spin coating, and epitaxial growth.

In a further aspect there is provided a crack structure, defined in claim 8.

The crack structure comprises a substrate and a spacer material layer on the substrate having at least one open space. There is a layer of one or more selected material(s) provided on the spacer material, the material layer being patterned to exhibit a crack-defined gap between two cantilevering parts extending across said open space, wherein the width of the crack-defined gap is predetermined by the length of the cantilevering parts and by the built-in stress. Optionally said cantilevering parts are collapsed onto the substrate. The crack is preferably less than 100 nm wide, preferably less than 3 nm wide thereby forming a tunnelling junction.

The conductive material is suitably selected from the group consisting of gold, platinum, single or few-layer graphene, titanium nitride, and superconducting materials, preferably provided by deposition techniques including, any of atomic layer deposition (ALD), sputtering, evaporation, chemical vapor deposition (CVD), layer transfer, spray coating, spin coating, and epitaxial growth.

In still a further aspect there is provided a method of making a tunnelling device for DNA sequencing, defined in claim 13. It comprises providing a substrate and making a membrane covering an opening in said substrate. A pore is made in said membrane the size of the pore being in the nm range, preferably <50 nm in diameter, such as 2-40 nm. The sacrificial material layer is deposited on at least one side of the substrate. A layer of one or more selected material(s), including at least one electrically conducting material, is deposited on the sacrificial layer on the side of the substrate where the membrane is located, such that there will be a residual stress in the deposited material. The electrode layer is patterned to provide a notched electrode bridge having one or several stress concentration structures, preferably a notch or notches located opposite each other along longsides of said electrode bridge or grooves extending across the bridge. Sacrificial material on the membrane side of the substrate is etched away at least beneath part of the electrode bridge, and all sacrificial material on the cavity side of the substrate is etched away, whereby the electrode bridge will crack at the stress concentration structure(s) due to release of the built-in stress, thus defining a nanogap tunnelling crack structure. However, it is possible to set the built-in stress such that the crack forms before etching away the sacrificial layer. The built-in stress can also be set such that the crack forms only after the sacrificial layer has been etched away.

The membrane is suitably made by providing a mask layer on one side of the substrate said mask layer having an opening exposing the substrate material, and etching away substrate material in said opening to form a cavity until a thin membrane remains at the bottom of the cavity.

The method further suitably comprises collapsing the cantilevering parts of the crack structure over the nanopore such that the free ends of the cantilevering parts contact the substrate thereby covering the pore such that the free ends of the cantilevering parts form a gap entrance to the pore.

In preferred embodiments before etching away the sacrificial material the method comprises depositing a further sacrificial material layer on the electrode material layer, depositing a further electrode material layer on said further sacrificial material layer, and patterning said further electrode material to define a further notched electrode bridge having notches located opposite each other along longsides of said electrode bridge, being oriented perpendicularly or rotated by another suitable angle to the previous electrode bridge.

In preferred embodiments after etching away the sacrificial material the method comprises depositing a further sacrificial material layer on the electrode material layer, depositing a further electrode material layer on said further sacrificial material layer, and patterning said further electrode material to define a further notched electrode bridge having notches located opposite each other along longsides of said electrode bridge, being oriented perpendicularly or rotated by another suitable angle to the previous electrode bridge, and further etching away sacrificial material at least beneath part of one of the bridges, and further forming a crack at the stress concentration structure(s), wherein the width of the crack-defined gap is predetermined by the length of the bridge and the built-in stress;

In still another aspect there is provided a tunnelling device for nanopore Sequencing.

Thus, the method of making a tunnelling device for nanopore sequencing, comprises the steps of providing a substrate; making a membrane covering an opening in said substrate; making a pore in said membrane the size of the pore being in the nm range, preferably <50 nm in diameter, such as 2-40 nm; depositing a sacrificial material layer on at least the membrane side of the substrate; depositing a layer of one or more selected material(s) on the sacrificial layer on at least one side of the substrate including at least one electrically conductive material, such that there will be a built-in stress in the material(s); patterning the layer(s) of selected material(s) to provide an electrode bridge having at least one stress concentration structure, preferably a notch or notches located opposite each other along longsides of said electrode bridge or as grooves extending across the bridge; etching away sacrificial material at least beneath part of the electrode bridge, and all sacrificial material on the cavity side of the substrate, forming a crack in the electrode bridge at the stress concentration structure(s)due, thus defining a nanogap tunnelling crack structure.

The device is defined in claim 19 and comprises a substrate having a membrane with a pore therein with a diameter in the range <50 nm, preferably 2-40 nm; at least one spacer material layer on the substrate having at least one open space; a layer of one or more selected material(s) provided on the spacer material, including at least one electrically conductive material, such that there will be a built-in stress in the material(s); the layer being patterned to exhibit a crack-defined gap between two cantilevering parts in the transverse direction thereof, extending across said open space and said pore, wherein the width of said crack is predetermined by the length of the cantilevering parts and by the built-in stress; and whereby the gap is <3 nm wide, and the conductive material in the electrode material layers form tunnelling electrodes.

The method enables wafer level production of a large number of devices on one wafer that can either be used in a matrix type system, using the entire wafer, or where the individual devices can be singulated into single sensor elements.

With the invention the width of a gap can be tailored in a range between sub-2 nm and >100 nm. The width of gap can be controlled for individual crack structure on a substrate by adjusting the length of the bridge structure. Bridge structures can be manufactured using wafer-scale compatible processes so that millions of crack structures can be produced on a single chip. The invention furthermore provides gaps having high gap-height vs gap-width aspect ratio. The cracked surfaces are free from contaminants introduced after deposition of the materials, and have perfectly matching geometries. Manufacturing can be applied on top of fully processed CMOS wafers, and can be applied to wide range of materials such as crystalline or amorphous materials, superconducting materials, and noble metals. The crack junction devices can be individually electrically connected to the CMOS circuits in a way that for each device the electron tunneling current can be measured in dependence of the sensing agent present in or near the nanogap of the tunneling junction device, with many devices being read out in a highly parallel fashion.

Further scope of applicability of the present invention will become apparent from the detailed description given hereinafter and the accompanying drawings which are given by way of illustration only, and thus not to be considered limiting on the present invention, and wherein FIG. 1 illustrates providing stress concentration structures;

DETAILED DESCRIPTION OF PREFERRED EMBODIMENTS

Generally the invention provides a method of making a crack structure in or on a substrate, said crack structure being usable as a i.a. tunnelling junction structure in a nanogap device. Such nanogap devices are in turn usable in a number of applications, notably in devices for so called quantum sequencing of DNA, RNA, and peptides molecules.

The method comprises the controlled fracture of patterned, suitably films under built-in stress, thereby forming elements, e.g. cantilevering parts or electrodes, separated by crack-defined nanogaps. By design of the length of the bridge in a range between sub-μm to >25 μm, the separation between the cantilevering parts can be controlled for each individual crack structure from <2 nm to >100 nm. The resulting nanogaps can feature very high gap-height to gap-width aspect-ratios of >20, perfectly matching cracked surfaces, and can be used as tunneling devices when the cantilevering parts are electrodes separated by sub-3 nm gaps.

In a first step in one embodiment of the method a thin film is placed under built-in stress on top of a sacrificial layer on a substrate. As substrates preferably Si, silicon carbide, glass, quartz, sapphire, GaAs, GaN, InP, and polymer, are usable, more preferably single crystal Si containing CMOS integrated circuits. Sacrificial materials can be selected i.a. from $Al_2O_3$, Si, SiO2, SiN, Al, single or few-layer graphene, and polymer, preferably provided by deposition techniques including, any of atomic layer deposition (ALD), sputtering, evaporation, chemical vapor deposition (CVD), layer transfer, spray coating, spin coating, and epitaxial growth. The thin film can be selected i.a. from gold, platinum, single or few-layer graphene, titanium nitride, and superconducting materials, preferably provided by deposition techniques including, any of atomic layer deposition (ALD), sputtering, evaporation, chemical vapor deposition (CVD), layer transfer, spray coating, spin coating, and epitaxial growth.

Figure 1:
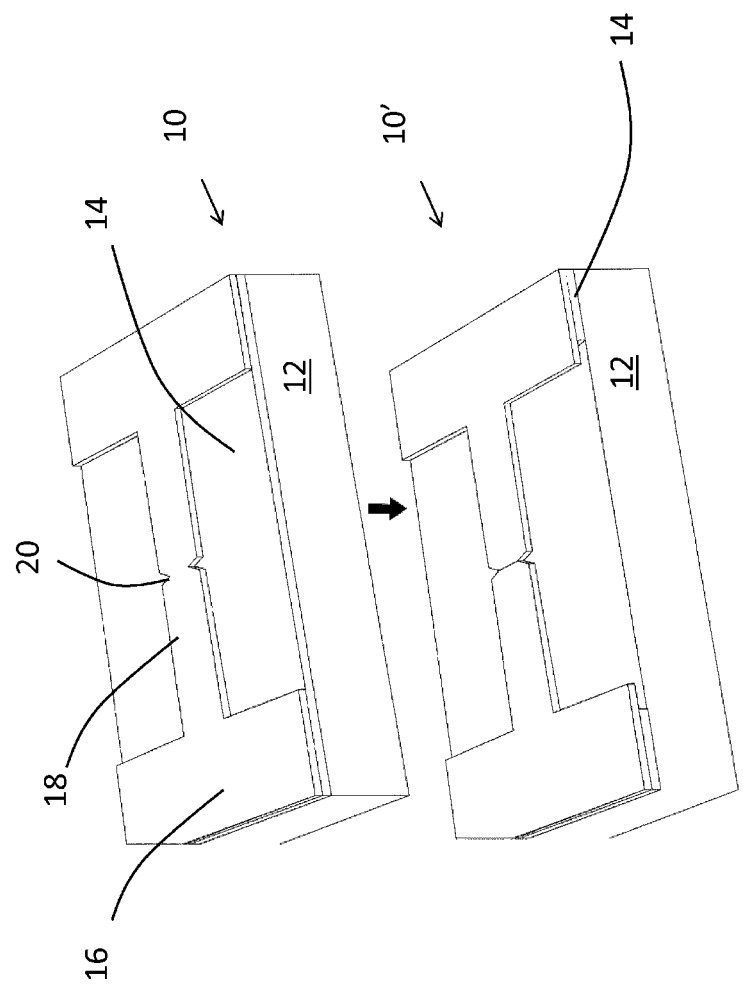

The thin film is patterned, suitably by lithographic techniques well known to the skilled man, to outline a bridge having one or several stress concentration structures, preferably a notch or notches provided in opposite positions along the extension of the bridge, as illustrated in FIG. 1. FIG. 1a shows a notched structure 10 before and FIG. 1b a structure 10' after crack formation. The structure 10 thus comprises a substrate 12, a sacrificial layer 14, a film 16 patterned to exhibit a bridge 18 having notches 20 on the longsides thereof.

Figure 2:
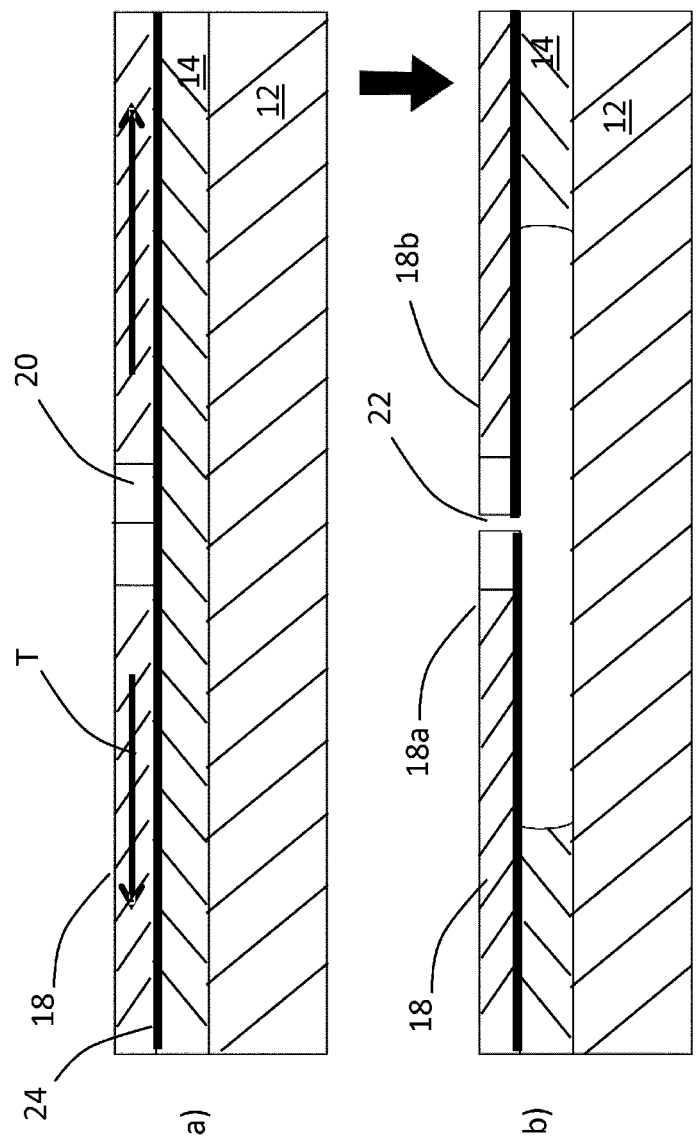
FIG. 2 is a cross section view of the structure in FIG. 1.

FIG. 2 shows the same structures as in FIG. 1 but in cross section. Thus, after patterning, the sacrificial material 14 supporting the electrode bridge 18 is selectively removed using isotropic chemical etching as shown in FIGS. 2a and b. In so doing, the conductive thin film 18 is locally detached from the substrate 12 and the built-in stress T (illustrated with arrows) that is stored in the thin film 18 is released. This, in turn, causes the build-up of stress in the film at the notch 20 of the electrode bridge. At any point during the process, once the local stress level at the notch overcomes the strength of the thin film material, a crack is initiated at the notch. The fracture of the electrode bridge allows, as a result of the built-in stress, contraction of the thin film electrodes in opposite directions and the formation of a nanoscale gap 22 that is separating the electrodes 18a, 18b as illustrated in FIGS. 2a and b.

By providing an electrically insulating material 24 beneath the electrode film 18, the electrodes are electrically isolated. This is further illustrated in FIG. 4c wherein it can be seen how the actual electrode material 26, e.g. gold or graphene, or some other preferred conductive material, is arranged between dielectric layers 28, e.g. SiN or some other preferred dielectric or insulating material, such as oxides.

The nanogap width is defined by the extent of the contraction w of the cantilevering parts, which is predetermined by the length L of the release-etched part of the bridge, on the built-in stress σ in the electrode film and on the Young's Modulus of the electrode material. In a first order approximation, the nanogap width is then defined by $w=(\sigma/E)*L$. Because of this proportionality between w and L, the nanogap width w can be varied for different devices placed on the same substrate simply by varying L. Thus, the method is based on the conversion of a μm-scale length that can be easily defined by standard lithographic patterning, to define a precisely controlled nm-scale separation between cantilevering parts, where σ/E is the conversion factor.

Figure 3:
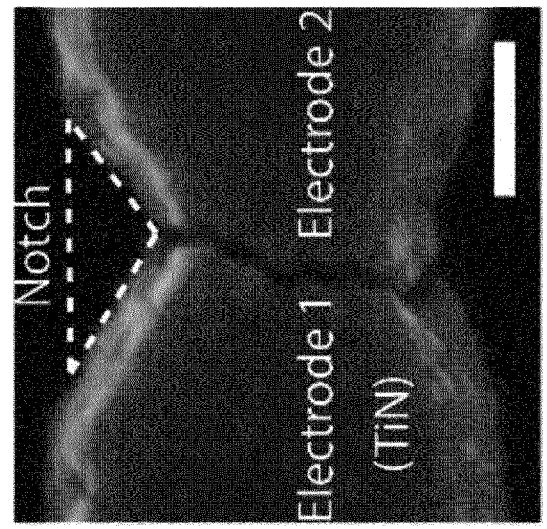
FIG. 3 are SEM images showing crack structures.
Figure 3:
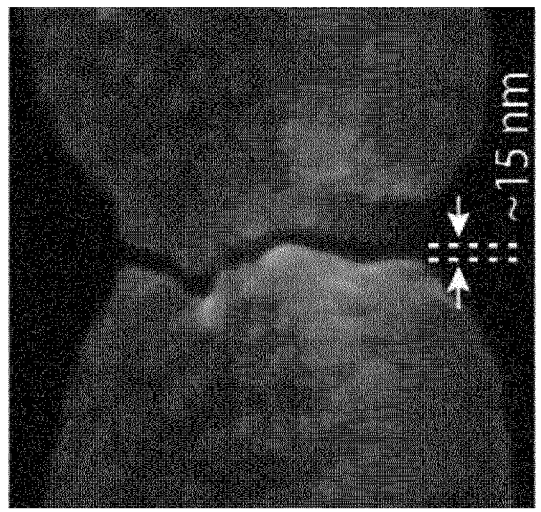

In one embodiment, the method is demonstrated by making electronic nanogaps in thin-film titanium nitride (TiN) electrodes that are placed on top of an aluminum oxide (Al2O3) sacrificial layer on a silicon (Si) substrate. TiN is a good electrode material because of its attractive structural, plasmonic and superconducting properties, which makes it a very promising electrode material for a variety of nanogap-based devices and applications. TiN features two additional relevant characteristics. Firstly, thin TiN films under residual tensile stress can be easily deposited on silicon substrates. This is achieved here by depositing a TiN film at a temperature of 350° C. When cooling the substrate after film deposition from 350° C. to room-temperature, the TiN film with a coefficient of thermal expansion (CTE) of 9.6×10-6 K-1 contracts to a larger extent than the silicon substrate with a CTE of 2.6×10-6 K-1, thus resulting in residual tensile stress in the TiN film. Secondly, TiN is a brittle material that does not exhibit substantial plastic deformation during fracture, which is a feature that facilitates crack propagation. A representative example of a crack-defined electronic nanogap featuring a gap width of 15 nm, a gap length of 120 nm and an electrode thickness of 100 nm is shown in FIGS. 3a and b. The suspended TiN cantilevers are straight and display sharp, vertically cracked surfaces that follow the grain boundaries of the TiN film. The low roughness of the cracked surfaces in the vertical direction is a result of the columnar structure of deposited TiN films.

The method enables large-scale fabrication of nanogaps separating conductive or non-conducting cantilevering parts, with gap widths that can be precisely controlled for each individual crack structure on a substrate. The crack formation in the thin film and definition of the separation between the cantilevering parts relies on built-in stress stored in the film, which can easily be tailored on a wafer by using film electrode and substrate materials with different CTEs (Coefficient of Thermal Expansion) and by adjusting the thin film deposition temperature. Furthermore, the bridge material may be brittle during crack-formation, which is the case for metals featuring a body-centered cubic (bcc) structure at low temperature. Thus, the method described here can be extended to other classes of materials featuring interesting mechanical, electronic, optical, superconducting or magnetic properties. For instance, amorphous (e.g. metallic glasses) or single crystalline (e.g. strained semiconductors) materials that are devoid of grain boundaries could be employed as material. Thus, crack propagation along grain boundaries could be avoided, thereby forming smoother cracked surfaces with even better control of the width of the crack-defined gap. Furthermore, since all fabrication processes employed in the present work are compatible with pre-fabricated complementary metal-oxide-semiconductor (CMOS) wafers, the crack-junctions can be integrated with CMOS circuits, thereby providing a path towards complex heterogeneous systems.

Example

Figure 4:
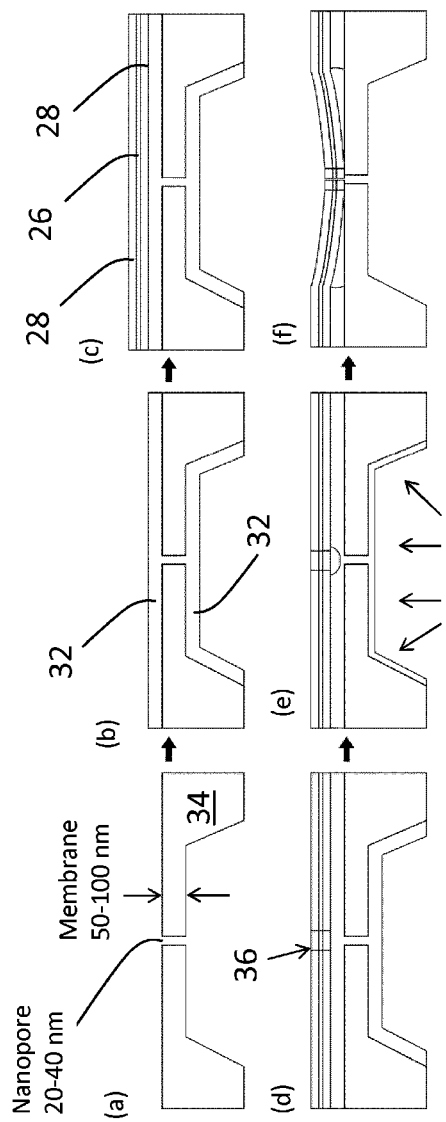
FIG. 4 illustrates a process.

The crack-junction method is illustrated by the process sequence in FIG. 4. In the crack-junction method, a conductive, suitably metallic, thin film 26, suitably provided between dielectric layers 28, under built-in stress is placed on top of a sacrificial layer 32 on a substrate 34 and patterned to outline a notched 36 electrode bridge as depicted in FIG. 3d. Next, FIG. 4e, the sacrificial material 32 supporting the electrode bridge is selectively removed using isotropic chemical etching, illustrated by arrows. In so doing, the thin film 26 is locally detached from the substrate and the tensile stress that is stored in the thin electrode film is released. This, in turn, causes the build-up of stress in the film at the notch of the electrode bridge. The initiation of a crack at the notch allows contraction of the thin film electrodes in opposite directions, and the formation of a nanoscale gap 38 that is separating the electrodes as illustrated in FIG. 4f. However, it is possible to set the built-in stress such that the crack forms before etching away the sacrificial layer. The built-in stress can also be set such that the crack forms only after the sacrificial layer has been etched away. The resulting width of the crack-defined nanogap can be tailored by defining the length of the release-etched part of the electrode bridge and by the built-in stress, i.e. the electrodes are contracting after crack formation between 0.1 to 100 nm for every 1 µm length of the suspended electrode bridge.

In one of the more advanced device designs, sub-3 nm wide nanogap electrodes made of one or two layers of graphene (~0.34-1 nm thick) are integrated with nanopores. FIG. 4a-f discussed above also depicts the process sequence wherein a nanopore with a diameter of about 20-40 nm is formed in a silicon nitride (SiN) or passivated silicon (Si) membrane 40 with a thickness of the order of 1-100 nm, using either electron-beam (e-beam) lithography or focused ion beam (FIB) milling, FIG. 4a. Thereafter, FIG. 4b, as in the process described above, a sacrificial layer is deposited on the substrate surface and inside the pore thus closing the pore, preferably using atomic layer deposition (ALD). Next, a stack of SiN/graphene/SiN is deposited and an electrode bridge is formed over the nanopore using lithography in combination with etching as depicted in FIG. 4c. After the sacrificial layer is etched, FIG. 4e, and the crack junction is formed, the electrodes are collapsed over the nanopore as indicated in FIG. 4f, thereby covering the nanopore and leaving a 1-2 nm wide nanogap over the pore, through which molecules can translocate. Compared to other techniques, the required dimensional and placement accuracies for the nanopores are in this approach significantly less demanding since the translocation channels are defined by the nanogaps. Thus, the dimensions of the nanopore can be on the order of 2-100 nm in diameter. Furthermore, the achievable high aspect ratio of the crack-defined nanogaps (gapheight vs gapwidth of up to 70, even for nanoscale dimensions) may be utilized to slow down the DNA translocation speed, which is a major challenge for all nanopore sequencing techniques. In an alternative concept, it is possible to form a nanopore by collapsing two stacked crack junctions that are rotated by an angle with respect to each other, thereby further limiting the possible path for a molecule to a narrow channel. Collapsing the electrodes can be easily achieved using stiction effects that are well-known during drying.

In still another aspect there is provided a tunnelling crack junction with a vertical graphene electrode is integrated in a flow channel. Such a configuration would have the advantage that all microfluidic channels and connectors can be easily integrated in the front side of the device.

Application

DNA sequencing based on the detection of analytes with tunnelling currents (quantum sequencing) is one of the most promising approaches, with the potential to increase the rate of detection by two or three orders of magnitude beyond what is possible with today's systems. Quantum sequencing methods further have the advantage that that the key components of the sequencing system may be realized using complementary metal-oxide-semiconductor (CMOS) and other solid-state technologies. They also potentially can achieve real-time single-molecule detection with little sample preparation, resulting in inherently low cost. In one promising device configuration for quantum sequencing, nanogap electrodes with electrode distances of less than 3 nm are integrated within nanopores. When single-stranded DNA (or RNA or peptide) molecules move across the nanopores, the tunnelling currents passing between the electrodes can be measured. On average, tunnelling currents differ for each type of nucleotide because of the different molecular electronic structures. It has been theoretically predicted, and experimentally demonstrated with functionalized scanning tunnelling microscope (STM) tips, that each DNA nucleotide carries a unique, statistically identifiable signature in the associated tunnelling current. However, there are a number of key technical challenges in quantum sequencing that have not yet been solved, including the realization of nanogap electrodes with electrode thicknesses of less than 1 nm and 1-2 nm wide nanogaps, and their integration in nanopores. Furthermore, the reliable and scalable fabrication of large numbers of such structures remains a major challenge.

At present, nanopores can be classified as either biological nanopores, solid-state nanopores or nanogap electrodes embedded in solid-state membranes. Solid-state pores can offer more durability than biological pores. In addition, solid-state nanopores offer compatibility with complementary metal-oxide-semiconductor (CMOS) technology and therefore industrial scalability, which could significantly reduce costs. With nanopore methods, very long strands (on the order of hundreds of thousands of bases or more) of DNA and RNA can be translocated through the channels with ease. However, for sequencing, the approach also requires a method to directly read the physical differences of individual nucleotides in a strand. Two 'principal axes' can be identified in DNA and RNA molecules: longitudinal and transverse. Oxford Nanopore Technologies have already developed biological nanopore-based sequencers that are based on longitudinal ionic transport.

However, the physics of longitudinal ionic transport through a small pore imposes a fundamental limit on resolution. Therefore, alternative approaches such as sequencing methods based on electron tunnelling are pursued. A number of different electrode configurations with sub-3 nm electrode distances have been proposed for evaluating sequencing by electron tunnelling. These include STM-based nanogap electrodes, various types of break-junction (BJ)-based nanogap electrodes, and nano-scale metal/dielectric/metal-stacks with exposed side-walls (used e.g. for recognition tunnelling). It is important to note that all solid-state devices face major manufacturing challenges related to precise control of the device dimensions. Likewise, for quantum sequencing devices based on nanogap electrodes that are integrated with nanopores, key difficulties include manufacturing scalability and the integration of nanoscale electrodes that are located transverse to a nanoscale channel.

In addition to the controlled fabrication of tunnelling devices, there are other very important challenges in quantum sequencing, including: (1) The thickness of the tunnelling electrodes should be at least as thin as the distance between individual bases of the DNA to be able to resolve individual DNA bases; (2) The tunnelling current signals in response to DNA translocation are extremely small and noisy; and (3) The variability and high speed of DNA translocation through nanopores further complicates the extraction and identification of useful tunnelling signals. A detailed discussion of state-of-the-art and short-comings of existing devices for quantum tunnelling are provided in [Di Ventra, Massimiliano, and Masateru Taniguchi. "Decoding DNA, RNA and peptides with quantum tunnelling." Nature nanotechnology 11.2 (2016): 117-126.].

For molecular detection and sequencing applications, the nanogap electrodes should preferably be made of gold to simplify surface functionalization or of ultra-thin graphene layers to provide the spatial electrode dimensions for resolving individual bases (monolayer graphene is about 0.34 nm thick). Thus, crack junctions with electrodes made of stacks of dielectric/Au/dielectric and dielectric/graphene/dielectric are of particular interest.

By built-in stress in a material is meant any stress resulting of any of residual stresses, mechanical strains, intrinsic stresses, and thermal stress in a material.

The sacrificial layer can be identical to the substrate material, to the membrane material, or any material below the bridge that can be selectively etched away in order to release the bridge structure, or expressed differently, the substrate material or membrane material can act as sacrificial material. The sacrificial layer can also consist of a combination of materials. The sacrificial layer can also consist in at least one layer(s) of at least one material(s) that is patterned, etched, or planarized.

The spacer layer can be considered as part of the substrate, part of the membrane, part of the bridge, or expressed differently that part of the substrate, part of the membrane or part of the bridge, can act as spacer layer.

By nanopore sequencing is meant including any of DNA, RNA, and peptides sequencing.

Numerous other applications of the novel crack structure and method of making are possible. For example there is provided a method of making nanowires, which comprises using a crack structure as disclosed herein in claims 7-12 as a shadow mask on a suitable substrate, said mask defining the nanowire.

Another application is a crack structure/pore structure, comprising at least one crack structure as disclosed herein, wherein the crack structure is placed on top of a pore.

A still further application is a crack-junction/flow channel structure, comprising at least one crack structure as disclosed herein, in which the crack-junction is placed in a flow channel.

The disclosed crack junctions can also be used for gas sensing, e.g. bio molecule sensing/DNA detection, using tunnelling currents that depend on the composition of the elements in the nanogap.

In an alternative embodiment the crack junctions disclose herein the electrode is placed in vertical direction to the electrode bridge.

The invention claimed is:

1. A crack structure on a substrate, comprising:
a substrate;
a layer of sacrificial material, located on the substrate and having an open space;
a layer of selected material (s) provided on the layer of sacrificial material, the layer of selected material (s) being patterned to exhibit a crack-defined gap between two cantilevering parts extending across said open space, a width of the crack-defined gap predetermined by a length of the cantilevering parts and by built-in stress in the material(s);
a space material layer, located on the layer of selected material(s) and having at least one further open space; and
a further layer of one or more selected material(s) provided on the spacer material layer, the further layer of selected material(s) being patterned to exhibit a further crack-defined gap between further cantilevering parts in a transverse direction thereof, extending across said further open space and said defined gap perpendicularly or rotated by another angle, a width of said further crack-defined gap predetermined by a length of the further cantilevering parts and by the built-in stress.

2. The crack structure according to claim 1, wherein the width of the crack-defined gap is less than 100 nm.

3. The crack structure according to claim 2, wherein the width of the crack-defined gap is less than 3 nm.

4. The crack structure according to claim 2, wherein characteristics of the tunneling currents of a tunneling junction formed by the width of the crack-defined gap depend on the type and/or composition of the elements in the crack-defined gap, for gas sensing, bio molecule sensing/DNA detection.

5. The crack structure according to claim 1,
wherein the layer of selected material(s) comprises a stacked structure of one or more electrically conductive layers separated by one or more dielectric layers.

6. The crack structure according to claim 5, wherein the conductive material consists of gold, platinum, single or few-layer graphene, titanium nitride, and superconducting materials.

7. The crack structure according to claim 1, wherein the substrate is made from a material selected from the group consisting of Si, silicon carbide, glass, quartz, sapphire, GaAs, GaN, InP, and polymer.

8. The crack structure according to claim 7, wherein the substrate is a single crystals wafer containing CMOS integrated circuits.

9. The crack structure according to claim 1, wherein the material in the sacrificial material layer is selected from the group consisting of $Al_2O_3$, Si, $SiO_2$, SiN, Al, single or few-layer graphene, and polymer.

10. The crack structure according to claim 9, wherein the sacrificial material is provided by deposition techniques including, any of atomic layer deposition (ALD), sputtering, evaporation, chemical vapor deposition (CVD), layer transfer, spray coating, spin coating, and epitaxial growth.

11. The crack structure according to claim 1, wherein the crack-defined gap is placed on top of a pore.

12. The crack structure according to claim 1, wherein the crack-defined gap is placed in a flow channel in such a way that at least part of the liquid flowing through the flow channel passes through the crack-defined gap.

13. The crack structure according to claim 1,
wherein said cantilevering parts and further cantilevering parts are collapsed onto one another thereby defining a pore at the interface between the two crack-defined gap and the further crack-defined gap.

* * * * *